US006861067B2

(12) United States Patent
McGhee et al.

(10) Patent No.: US 6,861,067 B2
(45) Date of Patent: Mar. 1, 2005

(54) HYDROGEL WOUND DRESSING AND THE METHOD OF MAKING AND USING THE SAME

(75) Inventors: Diane McGhee, Hazelwood, MO (US); Yeong Hua Huang, St. Louis, MO (US); Stephen B. Earhart, St. Louis, MO (US); William R. Fiehler, Maple Grove, MI (US)

(73) Assignee: Sherwood Services AG (CH)

( * ) Notice: Subject to any disclaimer, the term of this patent is extended or adjusted under 35 U.S.C. 154(b) by 260 days.

(21) Appl. No.: 09/772,801

(22) Filed: Jan. 30, 2001

(65) Prior Publication Data

US 2001/0026810 A1 Oct. 4, 2001

Related U.S. Application Data

(63) Continuation-in-part of application No. 09/156,547, filed on Sep. 17, 1998, now Pat. No. 6,180,132.

(51) Int. Cl.[7] ........................ A61L 15/00; A61F 13/00
(52) U.S. Cl. .................... 424/445; 424/443; 604/304; 604/308
(58) Field of Search ................. 424/445, 443; 604/308, 304; 602/41, 42, 46, 48, 52, 53, 56

(56) References Cited

U.S. PATENT DOCUMENTS

| | | | | |
|---|---|---|---|---|
| 4,226,232 A | 10/1980 | Spence | ................. | 128/156 |
| 4,517,326 A | 5/1985 | Cordts et al. | ............... | 524/310 |
| 4,793,337 A | 12/1988 | Freeman et al. | ............ | 128/156 |
| 4,846,165 A | * 7/1989 | Hare et al. | .................. | 228/156 |
| 4,909,244 A | 3/1990 | Quarfoot et al. | ............ | 128/156 |
| 5,059,424 A | 10/1991 | Cartmell et al. | ............ | 424/443 |
| 5,112,618 A | 5/1992 | Cartmell et al. | ............ | 424/443 |
| 5,115,801 A | 5/1992 | Cartmell et al. | .............. | 602/48 |
| 5,160,328 A | 11/1992 | Cartmell et al. | ............ | 604/307 |
| 5,204,110 A | 4/1993 | Cartmell et al. | ............ | 424/443 |
| 5,219,325 A | 6/1993 | Hennink et al. | .............. | 602/41 |
| 5,932,200 A | * 8/1999 | Reich et al. | ................. | 424/65 |

FOREIGN PATENT DOCUMENTS

| | | | |
|---|---|---|---|
| EP | 0 107 915 A | 5/1984 | |
| EP | 0 122 035 A | 10/1984 | |
| EP | 0 304 536 A | 3/1989 | |
| EP | O 305 052 A | 3/1989 | |
| EP | 0 309 309 A | 3/1989 | |
| EP | 0 335 669 A | 10/1989 | |
| EP | 0 341 045 A | 11/1989 | |
| EP | 0 356 614 A | 3/1990 | |
| EP | 0 424 165 A | 4/1991 | |
| EP | 0 426 422 A2 | 5/1991 | |
| EP | 0 450 671 A1 | 10/1991 | |
| EP | 0 455 324 A1 | 11/1991 | |
| EP | 0 536 875 A1 | 4/1993 | |
| FR | A 2 392 677 | 12/1978 | |
| FR | A 2 542 201 | 9/1984 | |
| WO | WO 88/08 310 | 11/1988 | |
| WO | WO 90/03 155 | 4/1990 | |
| WO | WO 98/17215 | 4/1998 | ........... A61F/13/00 |
| WO | WO 99/13923 | 3/1999 | ........... A61L/15/00 |

\* cited by examiner

Primary Examiner—Thurman K. Page
Assistant Examiner—Isis Ghali
(74) Attorney, Agent, or Firm—Mark S. Leonardo; Brown Rudnick Berlack Israels LLP

(57) ABSTRACT

A hydrogel wound dressing which is highly absorptive, contours to a wound site, and maintains the wound in a moist state to promote healing thereof. The hydrogel wound dressing may also contain additives to prevent bacterial and fungal infections and to control wound odor.

30 Claims, No Drawings

HYDROGEL WOUND DRESSING AND THE METHOD OF MAKING AND USING THE SAME

CROSS-REFERENCE TO RELATED APPLICATIONS

This Patent Application is a Continuation-In-Part of U.S. application Ser. No. 09/156,547 filed Sep. 17, 1998, now U.S. Pat. No. 6,180,132, the contents of which are incorporated herein by reference in its entirety.

FIELD OF THE INVENTION

The present invention relates to a hydrogel wound dressing and a method of making and using the same. More particularly, the present invention relates to a flexible hydrogel wound dressing which is highly absorptive, contours to a wound site and maintains a wound in a moist state to promote healing thereof and the method of producing and using the same. The hydrogel wound dressing may also contain additives such as antibiotics and/or anti-fungals, and/or other organic compounds to prevent infection and to control odor.

BACKGROUND OF THE INVENTION

The treatment of draining wounds is a problem in the medical profession. Wound exudate such as blood, serum and purulent matter from a draining wound can lead to bacterial growth and delayed healing if not treated properly. Difficulties arise in maintaining wounds free of such wound secretions to allow for healing. Another concern in treating such draining wounds is that some believe that allowing a wound to heal in a slightly moist state may actually accelerate healing. Accordingly, the medical profession desires a means for maintaining draining wounds in a clean, moist protected state.

Currently, in an attempt to meet such wound treatment needs, there are wound exudate absorption compositions which are comprised of hydrogel materials in powder form. One example of such a powder material includes dextranomer beads. Dextranomer beads are hydrophilic spherical beads which are applied to a wound to absorb wound exudate. Disadvantages noted in using materials in powder form include difficulty in achieving even application, lumping and clumping of the material after application removing the material from a wound site without damaging newly formed tissues in the wound.

U.S. Pat. No. 4,226,232 discloses the blending of a hydrogel material with a liquid curing agent such as polyethylene glycol prior to introducing the material to a wound. A difficulty observed in the use of this material is that it can not be sterilized by irradiation due to the formation of free radicals within the gel material. These free radicals so formed within the gel material cause an instability of the hydrogel product thereby shortening the shelf life thereof.

U.S. Pat. No. 5,059,424 ("'424 patent") discloses a wound dressing comprising a backing member with an adhesive layer and a hydrogel material layer of 15–30% polyhydric alcohol, 8–14% isophorone diisocyanate prepolymer, 5–10% polyethylene oxide-based diamine, 0–1% salt and the balance water. Difficulties associated with the use of this wound product include the limitation of not being able to cut the dressing to a size appropriate for the particular wound site and still having the backing member intact. Additionally, the hydrogel material disclosed in the '424 patent lacks the necessary strength to be used and removed intact without the added support of the backing material.

The need exists for a sterile wound dressing which provides a size appropriate protective covering for a draining wound capable of absorbing exudate from the wound. It is also desirable to have a wound dressing suitable to protect a wound from debris and foreign matter capable of contaminating the wound. It is also desirable to have a wound dressing which cushions a wound from pressure. It is also desirable to have a wound dressing which does not adhere to new tissue forming in a wound. It is also desirable to have a wound dressing which maintains a wound in a slightly moist state to promote healing. It is also desirable to have a wound dressing which will prevent the occurrence of infection. It is also desirable to have a wound dressing which will maintain a wound in a moist state without promoting a fungal infection. It is also desirable to have a wound dressing which will aid in the elimination of wound odor.

SUMMARY OF THE INVENTION

An illustrative embodiment of the present invention relates to a transparent, insoluble hydrogel wound dressing capable of absorbing exudate from a draining wound without becoming adhered thereto. The subject wound dressing maintains a wound in a slightly moist state to promote healing of the wound while retaining its overall strength to allow for removal thereof in a unitary fashion.

The hydrogel wound dressing of the illustrative embodiment is a polyurethane hydrogel material comprising polyurethane prepolymer, deionized water, glycols, polyalkyldiamine and optionally an anti-fungal and/or an antimicrobial and/or a bacteriostatic agent, and/or an organic additives may be added.

The method of producing the hydrogel material of the illustrative embodiment involves hydrolysis and addition reactions to produce a three-dimensional cross-linked polyurethane hydrogel as described in more detail below. The resultant polyurethane hydrogel material is blended and cast molded to allow for complete gelatinization thereof in less than 180 minutes at room temperature. Gelatinization preferably begins within 30 to 40 minutes. The subject bubble-free hydrogel wound dressing is then optionally subjected to temperatures below 0° C. to remove excess water prior to packaging and sterilization using radiation sterilization or other suitable sterilization techniques known to those skilled in the art prior to distribution.

The hydrogel material of the illustrative embodiment may optionally contain a variety of additives such as antibiotic compounds. The inert properties of the hydrogel prevent any such additive from being released from the hydrogel. Additives such as antibacterial compounds are not released from the hydrogel and are only effective upon contact for the efficacious properties of the additives. The hydrogel may also contain various anti-fungal agents to prevent the occurrence of fungal infection while still maintaining a desirable moist environment. Additionally, the hydrogel may also contain organic additives for the added benefit of controlling wound odor.

DETAILED DESCRIPTION OF THE INVENTION

The polyurethane hydrogel wound dressing of the illustrative embodiment is capable of absorbing moisture from a wound site or other bodily fluids discharged from the body until the overall composition comprises approximately 70 percent to 99 percent water or fluid. The subject non-adhesive hydrogel dressing provides for moist wound healing, absorbs wound exudate, allows for relatively fewer dressing changes, allows for easy removal with no trauma to a wound, protects a wound from contamination and minimizes wound odor.

The polyurethane hydrogel material of the illustrative embodiment is generally produced by the formation of carbamate (urethane) linkages by the reaction of isocyanates with alcohols and by the formation of urea linkages through the reaction of isocyanates with water. These reactions are achieved by blending a polyoxyethylene-rich isophorone diisocyanate terminated oligomer, i.e., a polyurethane prepolymer, with a polyetherdiamine chain modifier having a predominately polyethylene oxide backbone and an approximate molecular weight between 500 and 5,000, deionized water, propylene glycol and polyethylene glycol in accordance with the following reactions:

Step 1

Prepolymer+Alcohol→Polyurethane+Unreacted Prepolymer

Step 2

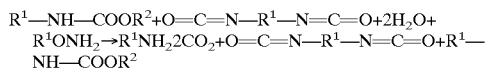

Polyurethane+Unreacted Prepolymer+Water+Amine Accelerator→ Polyamine(unstable intermediate)+Carbon Dioxide+Unreacted Prepolymer+Polyurethane Step 3

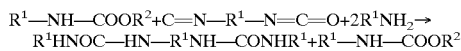

Polyurethane+Unreacted Prepolymer→Polyurea (stable)+Polyurethane+Polyamine (unstable intermediate)

Wherein the $R^1$ groups may be the same or different selected from the group consisting of $C_{1-12}$ alkyl repeating groups such as for example methyl, ethyl or propyl but preferably propyl for increased strength and stability; $C_{1-12}$ mono-or poly-hydroxyalkyl repeating groups such as for example hydroxymethyl or dihydroxypropyl but preferably dihydroxypropyl for increased strength and stability; $C_{1-12}$ acyl repeating groups such as for example acetyl or proprionyl but preferably proprionyl for increased strength and stability; $C_{1-12}$ alkoxyalkyl repeating groups such as for example methoxyethyl or ethoxypropyl but preferably ethoxypropyl for increased strength and stability; $C_{1-12}$ aminoalkyl repeating groups such as for example aminomethyl or aminopropyl but preferably aminopropyl for increased strength and stability; $C_{1-12}$ acylaminoalkyl repeating groups such as for example acetylaminomethyl or proprionylaminomethyl but preferably prorionylaminomethyl for increased strength and stability; $C_{1-12}$ oxyalkyl repeating groups such as but not limited to oxyethylene oxypropylene or oxybutylene but preferably oxyethylene and/or oxypropylene to increase clarity, such repeating units having an average molecular weight of about 7,000 to about 30,000 capped with aromatic, aliphatic or cycloaliphatic isocyanates, diisocyanates or polyisocyanates, but most preferably diisocyanate- or polyisocyanate-capped repeating units as described above having molecular weights of at least 10,000.

The use of aliphatic polyisocyanates is preferred in the illustrative embodiment to achieve a greater degree of handling freedom since aliphatic isocyanate-capped prepolymers typically require longer periods of time for gelatinization. In addition, aliphatic polyisocyanates will be preferred when the material is intended to be used in medical applications, because of increased biocompatability and decreased toxicological considerations. By contrast, prepolymers capped with aromatic polyisocyanates gelatinize in about 30 to 60 seconds as opposed to 20 to 90 minutes as typical for aliphatic isocyantes. Gelatinization within 30 to 60 seconds is a disadvantage for use in the present application due to a lack of adequate time for proper blending of the materials and molding thereof. The subject reaction mixture forms a hydrogel in approximately 15 to 180 minutes at room temperature but preferably in approximately 15 to 90 minutes. Gelatinization can also be accelerated if desired with the use of a standard curing oven. A preferred method of accelerating gelatinization has been found to include heating the composition at approximately 30 to 80 degrees Celsius for 5 to 40 minutes but more preferably at approximately 45 degrees Celsius for 30 minutes.

Examples of suitable dysfunctional and polyfunctional isocyanates include but are not limited to isophorone diisocyanate, toluene-2,4-diisocyanate, toluene-2,6-diisocyanate, mixtures of toluene-2,4, and 2,6-diisocyanate, ethylene diisocyanate, ethylidene diisocyanate, propylene-1,2-diisocyanate, cyclohexylene-1,2-diisocyanate, cyclohexylene-1,4-diisocyanate, m-phenylene diisocyanate, 3,3'-diphenyl-4,4'-biphenylene diisocyanate, 4,4'-biphenylene diisocyanate, 4,4'-diphenylmethane diisocyanate, 3,3'-dichloro-4,4'-biphenylene diisocyanate, 1,6-hexamethylene diisocyanate, 1,4-tetramethylene diisocyanate, 1,10, decamethylene diisocyanate, cumene-2,4-diisocyanate, 1,5-naphthalene diisocyanate, methylene dicyclohexyl diisocyanate, 1,4-cyclohexylene diisocyanate, p-tetramethyl xylylene diisocyanate, p-phenylenediisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenylether, 4,4'-diisocyanatodiphenylether, benzidine diisocyanate, 4,6-dimethyl-1,3-phenylene diisocyanate, 9,10-anthracene diisocyanate, 4,4'-diisocyanatodibenzyl, 3,3'-dimethyl-4,4'-diisocyanatodiphenylmethane, 2,6-dimethyl-4,4'-diisocyanatodiphenyl, 2,4-diisocyanatostilbene, 3,3'-dimethoxy-4,4'-diisocyanatodiphenyl, 1,4-anthracenediisocyanate, 2,5-fluorenediisocyanate, 1,8-naphthalene diisocyanate, 2,6-diisocyanatobenzfuran, 2,4,6-toluene triisocyanate, p,p',p"-triphenylmethane triisocyanate, trifunctional trimer of isophorone diisocyanate, trifunctional biuret of hexamethylenediisocyanate, trifunctional trimer of hexamethylene diisocyanate and polymeric 4,4'-diphenylmethane diisocyanate, but preferably diisophorone diisocyanate or isophorone diisocyanate for a preferred rate of gelatinization. Isophorone diisocyanate is utilized within the illustrative embodiment as a polyurethane pre-polymer because of its ability to completely react therefore leaving no unreacted IPDI groups. The absence of unreacted IPDI groups renders the hydrogel dressing inert. This inert nature of the hydrogel dressing prohibits the release of additive agents contained within the dressing preventing the systematic absorption of the additive agents.

$R^2OH$ is selected from the group consisting of $C_{1-12}$ monohydric alcohols such as ethanol, methanol or propanol, but preferably ethanol for improved biocompatability, $C_{1-12}$ diols such as alkyl glycols and derivatives thereof wherein propylene glycol is preferred for improved biocompatability, and $C_{1-12}$ polyalkyldiols such as polypropylene glycol, polyethylene glycol or polybutylene glycol wherein polyethylene glycol is preferred for better biocompatibility. Most preferably, propylene glycol and/or polyethylene glycol is used in the illustrative embodiment for biocompatability. Additionally, $R^2$ represents the corresponding $C_{1-12}$ alkyl group, such as methyl, ethyl or propyl but most preferably methyl for improved stability, $C_{1-12}$ hydroxyalkyl group such as hydroxy methyl hydroxyethyl or hydrooxypropyl but most preferably hydroxy methyl for improved stability, or $C_{1-12}$ polyhydroxyalkyl group derived from $R^2OH$ such as polyhydroxymethyl, polyhydroxyethyl, and polyhydroxypropyl but preferably polyhydroxymethyl for improved stability. The resultant clear or transparent product of the subject invention allows for undisturbed viewing of a wound for better wound care management.

The above noted chemical reactions illustrate the process by which the subject hydrogel is produced. In the initial step, as illustrated in STEP 1, an alcohol is reacted with a polyurethane prepolymer such as a isophorone diisocyate prepolymer but preferably a prepolymer of the following chemical composition:

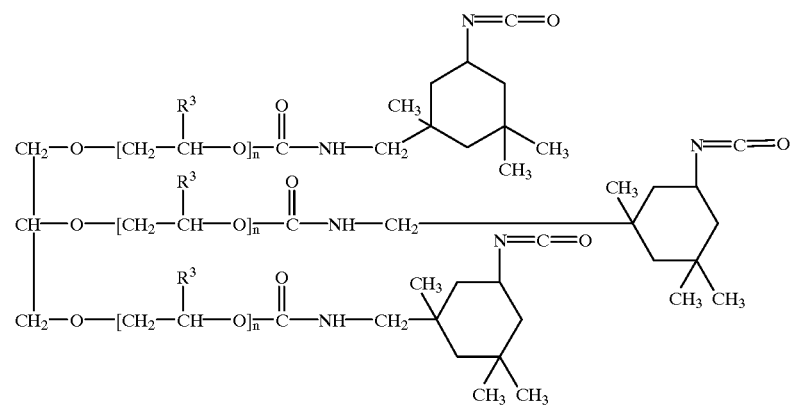

Wherein the $R^3$ groups may be the same or different selected from the group consisting of hydrogen and $C_{1-10}$ alkyl group such as for example methyl or ethyl but preferably methyl for improved stability; and n represents integers which may differ from one another within the range of 1 to 200. A mixture of hydrogen and methyl groups are the preferred $R^3$ groups for the above-described prepolymer in order to increase the flexibility and hydrophilicity of the final hydrogel product. The prepolymer is reacted with a $C_{1-12}$ alcohol, $C_{1-12}$ diol, $C_{1-12}$ alkyldiol and/or $C_{1-12}$ polyalkyldiol as described above, such as polyethylene glycol or propylene glycol in an alcoholsis reaction to form a polyurethane. Next, as illustrated in STEP 2 unreacted prepolymer further reacts with water and the polyalkoxyamine accelerator to undergo a hydrolysis reaction to form a polyamine and carbon dioxide. Due to the fact that the polyamine produced in STEP 2, is an unstable intermediate in this reaction process, STEP 3 illustrates the continued reaction of the polyamine of STEP 2, undergoing an addition reaction to form a stable polyurea. The rate of gelatinization for the polyurea is increased through the addition of the accelerator. Suitable accelerators include sodium carbonate, carbonate salts, sodium hydroxide, sodium citrate, potassium phosphate, ammonia, and polyalkoxyamines such as but not limited to polyetheramine due to its solubility and gelatinization acceleration capability. It has been found that such accelerators which are water soluble and have a molecular weight of preferably 200 to 5,000 improve polymerization rates. The series of reactions just described rather than producing a foam, results in a three-dimensional cross-linked polyurethane/polyurea hydrogel. It is important to note that water is added at the end of the second step of the procedure in order to prevent premature gelatinization and foaming. Additionally, the percentage of free isocyanate present in the prepolymer directly affects the gelatinization reaction rate. For this reason, in the illustrative embodiment the percentage of free isocyanate present in the reaction mixture is strictly controlled to a level below 5 percent to slow the reaction and slow gelatinization. Another consideration to be noted is that the faster the reaction rate, the faster the carbon dioxide gas is produced, which if not properly controlled causes the formation of a foam rather than a hydrogel. It is the control of these critical factors, i.e., the percentage of isocyanate present, the reaction rate and the gelatinization rate among the other considerations noted herein, which allows one to produce the unexpectedly superior hydrogel of the illustrative embodiment.

In order for one to achieve the desired reaction mixture of the illustrative embodiment and form a hydrogel of desirable strength and integrity for the intended use, STEP 1 involves blending together approximately 25 to 70 percent of the polyurethane prepolymer but preferably approximately 60.5 percent and approximately 30 to 75 percent of a polyalkyl diol such as polyethylene glycol but preferably approximately 39.5 percent to produce Product A. STEP 2 involves combining approximately 50 to 90 percent deionized water but most preferably approximately 74.2 percent, approximately 0.2 to 10 percent of a polyaikoxyamine such as polyetheramine but preferably about 1.6 percent to reduce production time by increasing the rate of gelatinization, and approximately 5 to 40 percent of an alkyl diol such as propylene glycol but preferably about 24.2 percent to produce Product B to react with Product A. Approximately 15 to 60 percent of Product A but preferably about 38.0 is blended with approximately 40 to 85 percent of Product B but preferably about 62.0 percent to produce the desired hydrogel wound dressing of the illustrative embodiment.

Optionally, 0–5% but preferably 1–3% of an antimicrobial or a bacteriostatic agent can be added to the final reaction mixture or Product B. Suitable such antimicrobial and bacteriostatic agents include but are not limited to: the biguanides, especially chlorhexidine and its salts, including chorhexidene acetate, chlorhexideine gluconate, chlorhexidine hydrochloride, and chlorhexidine sulfate, silver and its salts, including silver acetate, silver benzoate, silvercarbonate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampician, bacitracin, neomycin, chloramphenical, quinolone such as oxolinic acid, norfloxacin, nalidix acid, pefloxacin, enoxacin and ciprofloxacin, penicillins such as ampicillin, amoxicillin and piracil, cephalosporins, vancomycin, bismuth tribromophenate, and combinations of any of the above anti-microbials. These anti-microbial agents can be incorporated singularly or in combination or in combination with other additives.

Optionally, 0–5% but preferably 1–3% of an anti-fungal agent can be added to the final reaction mixture or Product B. Suitable anti-fungal agents include but are not limited to: Tolnaftate, Miconazole, Fluconazole, Econazole, Ketoconazole, Itraconazole, Terbinafine, and Polyene anti-fungal agents such as Amphotericin, Nystatin and Natamycin. These anti-fungal agents can be incorporated singularly or in combination with other additives.

Optionally, 0–5% but preferably 1–3% of an organic compounds can be added to the final reaction mixture or Product B. Suitable such organic compounds include but are not limited to: Grapefruit Seed Extract, Tea Tree Oil, Myrtle Oil, and Lemon grass extract. These organic compounds can be incorporated singularly or in combination with other additives In one illustrative embodiment bismuth tribromophenate or silver sulfadiazine are optionally added to the reaction mixture to decrease the risk of wound infection and odor. The resultant hydrogel wound dressing is characterized in that it comprises 5 to 30 percent by weight of a polyurethane prepolymer but most preferably 23 percent, 3 to 45 percent by weight of polyethylene glycols and propylene glycols but most preferably 30 percent and the balance water, accelerator and optional additives. The polyurethane hydrogel of the present invention is manufactured as further described in the following examples:

EXAMPLE A

Hydrogel Produced from Isophorone Diisocyanate based Prepolymer

Ten grams of isophorone diisocyanate prepolymer was mixed thoroughly with 10.0 grams of polyethylene glycol (Portion A). Then 30.0 grams of deionized water was mixed with 10.0 grams of propylene glycol and 0.5 grams of polyetherdiamine (Portion B). Portion A and Portion B were mixed thoroughly with a stirring rod for about two to 5 minutes until a homogeneous solution was formed. The solution was then cast into a 4"×4" mold coated with a silicone-polyethylene oxide polymer release agent and maintained undisturbed for 90 minutes at room temperature while the gelatinization reaction occurred. The mold was kept in a closed container at room temperature overnight to prevent water evaporation and to permit essentially complete chemical reaction of all isocyanate end groups. The final hydrogel upon removal from the mold was flexible, transparent and able to absorb 40 to 50 percent its own weight in one hour.

EXAMPLE B

Hydrogel Produced from Toluene Diisocyanate based Prepolymer

Five grams of polyethylene glycol was mixed with five grams of toluene diisocyanate prepolymer (Portion A). Then fifteen grams of deionized water was mixed with seven grams of propylene glycol and 0.7 grams of polyetherdiamine (Portion B). Portion A and Portion B were quickly mixed and cast into two aluminum weighing dishes coated with silicone-polyethylene oxide copolymer release agent. The material gelatinized within 30 minutes. Both dishes, filled with the hydrogel material, were kept in a closed container at room temperature overnight to prevent water evaporation and to permit essentially complete chemical reaction of all isocyanate end groups. The final hydrogel material, upon removal from the dishes, was flexible, transparent and able to absorb 40 to 50 percent its own weight in one hour.

EXAMPLE C

Hydrogel Produced with Bacteriostatic Agent Bismuth Tribromophenate (BTP)

A hydrogel with BTP was formed by repeating the preparation of Example A, except 0.6 grams of BTP was added to Portion B. The final hydrogel was flexible and able to absorb 40 to 50 percent its own weight in one hour.

EXAMPLE D

Hydrogel Produced with Antimicrobial Silver Sulfadiazine (SSD)

A hydrogel with SSD was formed by repeating the preparation of Example A, except 0.2 grams of SSD was added to Portion B. The final hydrogel was flexible and able to absorb 40 to 50 percent its own weight in one hour.

Once the subject hydrogel is blended as described in detail in the above Examples, the hydrogel may be cast and molded in any size or shape but is preferably molded into ropes having a length ranging from about two to twelve inches but preferably between four to eight inches and a width ranging from 0.1 to 2 inches but preferably about 0.25 to 1.75 inches or into disks having a diameter ranging between one and twelve inches but most preferably between two and six inches for ease of use. The thickness of the disks and ropes may vary substantially from 0.01 to 1 inch in thickness but most preferably are molded to 0.1 inch to 0.75 inch in thickness for ease of use with acceptable absorption.

The unexpected significant advantages of the present hydrogel dressing achieved through the particular reaction ratios noted above include increased absorption capabilities and increased strength. The increased strength of the subject hydrogel material eliminates the need for backing material as described in the prior art. Additionally, the hydrogel is stable, does not become brittle or crack with moisture loss, and has an extended shelf-life over other such materials.

The subject hydrogel dressing so produced is clear unless altered by additives such as bacteriostatic or antimicrobial agents and the like. Additive agents such as the silver salts will cause the resulting hydrogel dressing to discolor. The addition of other antibiotics, antifungals or organic additives either singularly or in combination may result in a less than desirable aesthetic appearance. Numerous organic dyes and inorganic pigments that are well known in the art may be added to the hydrogel improving the appearance of the dressing without affecting the function of the hydrogel.

After the hydrogel is cast, molded, and formed, which usually takes approximately one half hour to an hour at room temperature. The gelatinization time can be shortened by curing the hydrogel at a higher temperature. The hydrogel once formed may be exposed to low temperatures such as below 0° C. for approximately one half to four hours but preferably approximately one to two hours to extract excess water and to fully complete the reactions described above. This extraction of excess moisture significantly and unexpectedly increases the absorptive capabilities of the subject wound dressing which is capable of absorbing approximately 2 to 6 times its weight.

The subject hydrogel dressing is packaged and sterilized using an appropriate sterilization technique or may be sterilized and then packaged using aseptic technique. Appropriate methods of sterilization and packaging are known to those skilled in the art and include gamma radiation, electronic beam, ethylene oxide and like methods of sterilization. Preferably, the subject hydrogel wound dressing is packaged and then sterilized using gamma radiation by cobalt 60 with 1 to 3 mrads but preferably 2 mrads in two independent exposure cycles.

Appropriate packaging for the subject hydrogel wound dressing includes metallic foil pouches such as aluminum foil pouches, polyethylene film, ethylene vinyl acetate film, polypropylene film, polyvinyl chloride film, and like packages known to those skilled in the art.

The method of using the subject hydrogel wound dressing includes removing the dressing from its packaging and placing the dressing on or in a wound. Depending on the amount of exudate draining from a wound site, the dressing should be changed approximately every 1 to 2 days. The dressing in rope form can also be used for deep tunnel wounds. The dressing may be cut using aseptic technique to a size appropriate for a particular wound before placing the dressing on the wound. The dressing may also be formed into various geometric shapes and packaged for an assortment of uses by the consumer. These geometric shapes may include circular shapes that can be used by nursing mothers for the hydrogel's absorbent properties and additionally its cooling properties.

If after cutting the subject wound dressing the unused portion experiences water loss, the same may be rehydrated using aseptic technique and sterilized water.

It is seen therefore that the present hydrogel wound dressing provides an effective moist wound dressing to maintain draining wounds in a clean protected state. The wound dressing and method of making and using the same disclosed herein has specific advantages over the heretofore known means of treating draining wounds. The subject wound dressing eliminates risks associated with the treatment of draining wounds, lessens tissue damage upon removal thereof and may be cut to the appropriate size for ease of placement and use. Hence, for these reasons as well as others, some of which herein above set forth, it is seen that the present hydrogel wound dressing represents a significant advancement in the art which has substantial commercial significance.

Although the hydrogel material described in the illustrative embodiment herein is utilized in the treatment of wounds having exudate it should be appreciated that hydrogel material could be implemented to absorb bodily fluids that are not a result of a wound, such as milk from a lactating mother or urine in the incontinent patient, or the like. It should also be appreciated that the hydrogel can be used as a post operative dressing in procedures where the healing incision would benefit from a dressing having the properties of the hydrogel. Specifically, the hydrogel can be used as a post operative dressing for procedures such as breast augmentation, mastectomy and rhinoplasty. It can also be effectively used as a dressing in the treatment of chronic wounds such as diabetic ulcers. Similarly, rather than utilize the hydrogel material for its absorbent qualities the hydrogel material can be utilized for its ability to provide cooling properties to inflamed body areas. Additionally, rather than utilize the hydrogel material for human use it can be utilized for various veterinary applications. Conversely, the hydrogel material can be used for non-medical uses and incorporated into sportswear, such as headbands and wristbands, for both its absorptive and cooling properties.

While there is shown and described herein certain specific embodiments of the invention, it will be manifest to those skilled in the art that various modifications may be made without departing from the spirit and scope of the underlying inventive concept and that the same is not limited to the particular forms herein shown and described except insofar as indicated by the scope of the appended claims.

What is claimed is:

1. A self supporting resilient hydrogel composition comprising from 5 percent to 30 percent by weight of a polyurethane prepolymer, from 3 percent to 45 percent by weight of one or more polyalkyl diols selected from the group consisting of polyethylene glycol, polypropylene glycol and polybutylene glycol, from 3 percent to 45 percent by weight of one or more alkyl diols, and the balance water, accelerator and an additive; wherein the alkyl diols are selected from the group consisting of $C_{1-12}$ diols.

2. The hydrogel composition of claim 1 wherein said additive is an anti-microbial agent and is added to reduce wound odor and risk of infection when used as a wound dressing.

3. The hydrogel composition of claim 1 wherein said additive is an anti-fungal agent and is added to reduce wound odor and risk of fungal infection when used as a wound dressing.

4. The hydrogel composition of claim 1 wherein said additive is an organic additive agent and is added to reduce wound odor when used as a wound dressing.

5. The hydrogel composition of claim 2 wherein said anti-microbial agent is selected from the group consisting of chlorhexidene acetate, chlorhexideine gluconate, chlorhexidine hydrochloride, and chlorhexidine sulfate, silver acetate, silver benzoate, silvercarbonate, silver iodate, silver iodide, silver lactate, silver laurate, silver nitrate, silver oxide, silver palmitate, silver protein, and silver sulfadiazine, polymyxin, tetracycline, tobramycin, gentamicin, rifampician, bacitracin, neomycin, chloramphenical, oxolinic acid, norfloxacin, nalidix acid, pefloxacin, enoxacin, ciprofloxacin, ampicillin, amoxicillin, piracil, cephalosporins, vancomycin, and bismuth tribromophenate.

6. The hydrogel composition of claim 5 wherein said anti-microbial agents are in combination with each other.

7. The hydrogel composition of claim 3 wherein said anti-fungal agent is selected from the group consisting of Tolnaftate, Miconazole, Fluconazole, Econazole, Ketoconazole, Itraconazole, Terbinafine, Amphotericin, Nystatin and Natamycin.

8. The hydrogel composition of claim 4 wherein said organic additive agent is selected from the group consisting of Grapefruit Seed Extract, Tea Tree Oil, Myrtle Oil, and Lemon grass extract.

9. The hydrogel composition of claim 1 where said hydrogel composition further includes an organic dye.

10. The hydrogel composition of claim 1 wherein said hydrogel composition further includes an inorganic pigment.

11. The hydrogel composition of claim 1 wherein said additive is a combination of an antimicrobial, an anti-fungal, and an organic additive.

12. A method of producing a self supporting resilient hydrogel composition comprising:

forming a first solution of polyurethane prepolymer and a polyalkyl diol selected from the group consisting of polyethylene glycol, polypropylene glycol and polybutylene glycol;

forming a second solution of water, alkyl diol and accelerator;

adding an additive agent to either said first solution or said second solution; and combining said first solution with said second solution; wherein the alkyl diol is selected from the group consisting of $C_{1-12}$ diols.

13. The method of claim 12 wherein said additive agent is added to said first solution.

14. The method of claim 12 wherein said additive agent is added to said second solution.

15. The method of claim 12 wherein said additive agent is anti-microbial agent.

16. The method of claim 12 wherein said additive agent is an anti-fungal agent.

17. The method of claim 12 wherein said additive agent is an organic compound.

18. The method of claim 12 wherein said combined first and second solutions are cast, molded and heated.

19. The method of claim 12 wherein said combined first and second solutions are cast and molded to form a wound dressing approximately 0.01 to 1.0 inch thick.

20. The method of claim 12 wherein said combined first and second solutions are cast and molded to form a wound dressing in the shape of a disc with a diameter ranging from approximately 1.0 inch to 12.0 inches.

21. The method of claim 12 wherein said combined first and second solution do not contain an additive.

22. The method of claim 12 wherein said combined first and second solutions are cast and molded in the shape of a rope approximately 2 to 12 inches in length and 0.1 to 2.0 inches in width.

23. A self supporting resilient hydrogel composition comprising a polyurethane prepolymer, one or more alcohols selected from the group consisting of polyethylene glycol, polypropylene glycol and propylene glycol, an alkyl diol and the balance water, and an accelerator; wherein the alkyl diol is selected from the group consisting of $C_{1-12}$ diols.

24. The hydrogel composition of claim 23 wherein said hydrogel composition is cast and molded to form a dressing in the shape of a disc with a diameter ranging from approximately 1.0 inch to 12.0 inches.

25. The hydrogel composition of claim 24 wherein said dressing is used as a nursing pad for lactating mothers.

26. The hydrogel composition of claim 23 wherein said hydrogel composition is cast and molded to form a dressing in the shape of a rope approximately 2 to 12 inches in length and 0.1 to 2.0 inches in width.

27. The hydrogel composition of claim 26 wherein said dressing is used as a post operative dressing for rhinoplasty.

28. The self supporting resilient hydrogel composition of claim 23 wherein said hydrogel composition is cast and molded to form a dressing approximately 2 to 2.5 cm thick.

29. The hydrogel composition of claim 23 wherein said hydrogel is used as a post operative dressing for mastectomy patients.

30. The hydrogel composition of claim 23 wherein said hydrogel is used as a pant liner for incontinent patients.

* * * * *